United States Patent
Min et al.

(10) Patent No.: US 10,668,452 B2
(45) Date of Patent: Jun. 2, 2020

(54) METHODS AND MATERIALS FOR IMPROVED CATALYTIC OLIGOMERIZATION

(71) Applicant: INVISTA NORTH AMERICA S.A.R.L., Wilmington, DE (US)

(72) Inventors: Ji Min, Dalian (CN); An Bowen, Dalian (CN); Brian Clancy-Jundt, Wilmington, DE (US); William M. Cross, Wilmington, DE (US); Daniel Travis Shay, Wilmington, DE (US); Cai Tian Xi, Dalian (CN)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

(21) Appl. No.: 15/843,511

(22) Filed: Dec. 15, 2017

(65) Prior Publication Data

US 2018/0169627 A1 Jun. 21, 2018

Related U.S. Application Data

(60) Provisional application No. 62/436,041, filed on Dec. 19, 2016.

(51) Int. Cl.
| | | |
|---|---|---|
| C07C 2/24 | (2006.01) |
| B01J 23/83 | (2006.01) |
| B01J 23/94 | (2006.01) |
| B01J 38/04 | (2006.01) |
| B01J 37/12 | (2006.01) |
| B01J 37/08 | (2006.01) |
| B01J 37/02 | (2006.01) |
| B01J 37/16 | (2006.01) |
| B01J 38/02 | (2006.01) |
| B01J 23/00 | (2006.01) |
| B01J 21/06 | (2006.01) |
| B01J 21/04 | (2006.01) |

(52) U.S. Cl.
CPC ............ *B01J 23/83* (2013.01); *B01J 21/063* (2013.01); *B01J 23/002* (2013.01); *B01J 23/94* (2013.01); *B01J 37/0201* (2013.01); *B01J 37/0209* (2013.01); *B01J 37/0236* (2013.01); *B01J 37/08* (2013.01); *B01J 37/086* (2013.01); *B01J 37/088* (2013.01); *B01J 37/12* (2013.01); *B01J 37/16* (2013.01); *B01J 38/02* (2013.01); *B01J 38/04* (2013.01); *C07C 2/24* (2013.01); *B01J 21/04* (2013.01); *B01J 2523/00* (2013.01); *C07C 2521/04* (2013.01); *C07C 2521/06* (2013.01); *C07C 2523/83* (2013.01); *Y02P 20/127* (2015.11); *Y02P 20/52* (2015.11)

(58) Field of Classification Search
CPC .......... C07C 2/24; C07C 11/08; C07C 11/09; C07C 11/107; C07C 2521/04; C07C 2521/06; C07C 2523/83; B01J 21/063; B01J 23/755; B01J 23/83; B01J 23/94; B01J 37/0201; B01J 37/0236; B01J 37/08; B01J 37/12; B01J 37/16; B01J 38/04

See application file for complete search history.

(56) References Cited

U.S. PATENT DOCUMENTS

| | | | |
|---|---|---|---|
| 3,960,978 A | 6/1976 | Givens et al. | |
| 4,021,502 A | 5/1977 | Plank et al. | |
| 4,504,693 A | 3/1985 | Tabak et al. | |
| 4,511,750 A | 4/1985 | Miller | |
| 8,021,620 B2 | 9/2011 | Nicholas et al. | |
| 8,471,085 B2 | 6/2013 | Sydora | |
| 2009/0093657 A1* | 4/2009 | Buchanan | C10G 2/32 585/1 |
| 2010/0247391 A1* | 9/2010 | Nicholas | B01J 23/755 422/131 |

FOREIGN PATENT DOCUMENTS

WO  2004/000454 A1  12/2003

OTHER PUBLICATIONS

Yee et al., "Sensitivity Study of the Propane Dehydrogenation Process in an Industrial Radial Moving Bed Reactor", Journal of Engineering Science and Technology, 2014, pp. 62-74.

Kister et al., "Troubleshooting a C3 Splitter Tower Part 1: Evaluation", Digital Refining, 2014, pp. 97-103.

* cited by examiner

*Primary Examiner* — Sharon Pregler
(74) *Attorney, Agent, or Firm* — Licata & Tyrell P.C.; Robert B. Furr, Jr.

(57) ABSTRACT

Described herein are materials and methods for improved catalytic oligomerization of an ethylene monomer and/or propylene monomer. The present disclosure teaches oligomerizing the ethylene monomer or propylene monomer to produce oligomers. Also described is a heterogeneous catalyst comprising sulfate modified nickel on titanium modified alumina and a surface modification with yttrium (Y) suitable for use in the disclosed oligomerization.

12 Claims, 3 Drawing Sheets

METHODS AND MATERIALS FOR IMPROVED CATALYTIC OLIGOMERIZATION

This patent application claims the benefit of priority from U.S. Provisional Application Ser. No. 62/436,041, filed Dec. 19, 2017, the contents of which are herein incorporated by reference in their entirety.

TECHNICAL FIELD

This present disclosure relates to an oligomerization catalyst system, methods for preparing the oligomerization catalyst system, and methods for using the oligomerization catalyst system for preparing an oligomerization product. The present disclosure relates to processes for the catalytic oligomerization of ethylene and propylene into a butene, hexene, octene, or heavier olefinic compounds. The processes of the present disclosure utilize a heterogeneous catalyst comprising sulfate modified nickel on titanium modified alumina and a surface modification with yttrium (Y), the catalyst capable of the conversion of ethylene and/or propylene into one or more oligomers. The oligomer products produced by processes of the present disclosures are suitable for use for the manufacture of a variety of chemical products.

BACKGROUND

Oligomerization catalyst systems, methods for preparing such catalysts and methods for using such catalyst systems for preparing oligomerization products are known in the art, including processes and products for the catalytic oligomerization of ethylene and propylene. Such oligomerization catalyst systems, methods for preparing such catalysts and methods for using such catalyst systems for preparing oligomerization products have included complex, sensitive organometallic metal/ligand homogenous catalysts.

For example, conversion of olefins to gasoline and/or distillate products is disclosed in U.S. Pat. Nos. 3,960,978 and 4,021,502 wherein gaseous olefins in the range of ethylene to pentene, either alone or in admixture with paraffins, are converted into an olefinic gasoline blending stock by contacting the olefins with a catalyst bed made up of a ZSM-5 type zeolite.

U.S. Pat. No. 4,504,693 describes a process for converting feedstock comprising lower olefins to form higher hydrocarbons comprising a major amount of distillate product, wherein the olefinic feedstock is combined with a pressurized stream comprising olefins in the presence of a zeolite oligomerization catalyst under elevated temperature in a pressurized reactor zone. U.S. Pat. No. 4,504,693 describes a crystalline zeolite of the ZSM-5 type oligomerization catalyst for converting olefinic feedstocks containing $C_2$-$C_6$ alkenes at elevated temperature and pressure.

U.S. Pat. No. 4,511,750 describes a process for oligomerizing propylene and butenes, which includes use of a catalyst having nickel sulfate associated with a porous, refractory, inorganic oxide. In this process, the catalyst is contacted with a gas comprising oxygen at a temperature in the range from about 750 F to about 1150 F for at least 2 hours and contacting the resulting catalyst with an inert gas at a temperature of about 350 F to about 750 F for at least 1 hour.

U.S. Pat. No. 8,471,085 describes an olefin oligomerization system and process, including a catalyst having a transition metal compound and a pyrrole compound, wherein the pyrrole compound has a hydrogen atom at the 5-position or at the 2- and 5-position and a bulky substituent located on each carbon atom adjacent to the carbon atom bearing a hydrogen atom at the 5-position or the 2- and 5-positions, and a metal alkyl. According to U.S. Pat. No. 8,471,085, the productivity of certain oligomerization system and processes is acutely affected by variations in temperature.

Use of a catalyst in contact with ethylene in a dilute ethylene stream to produce heavier hydrocarbons has been described. For example, U.S. Pat. No. 8,021,620 describes a catalyst comprising an amorphous silica-alumina base, with a Group VIII and/or VIB metal, which catalyst is described as being resistant to hydrogen sulfide, carbon oxides, hydrogen and ammonia. As described in U.S. Pat. No. 8,021,620, a dilute ethylene feed is contacted with the oligomerization catalyst at a temperature between about 200° C. and about 400° C.

Thus, improved materials and methods for the oligomerization of ethylene and propylene in refinery streams are of interest.

SUMMARY

An aspect of this disclosure is related to a process for the catalytic oligomerization of an ethylene monomer. The process comprises providing a first stream comprising ethane and ethylene monomer and providing a heterogeneous catalyst comprising sulfate modified nickel on titanium modified alumina, and a surface modification with yttrium (Y). The process further comprises contacting the first stream and the heterogeneous catalyst under oligomerization conditions and oligomerizing the ethylene monomer in the first stream to produce an oligomer, the oligomer comprising one or more of a butene, hexene, octene, or a heavier olefinic compound, derivatives thereof or any combination thereof. In one nonlimiting embodiment, an oligomer stream is provided wherein the concentration of oligomer in the oligomer stream is greater than the concentration of oligomer in the first stream.

Another aspect of this disclosure is related to a process for the catalytic oligomerization of a propylene monomer. The process comprises providing a first stream comprising propane and propylene monomer and providing a heterogeneous catalyst, the heterogeneous catalyst comprising sulfate modified nickel on titanium modified alumina, and a surface modification with yttrium (Y). The process further comprises contacting the first stream and the heterogeneous catalyst under oligomerization conditions and oligomerizing the propylene in the first stream to produce an oligomer, the oligomer comprising one or more of a hexene, nonene, or a heavier olefinic compound, derivatives thereof or any combination thereof. In one nonlimiting embodiment, an oligomer stream, wherein the concentration of oligomer in the oligomer stream is greater than the concentration of oligomer in the first stream.

Another aspect of this disclosure is related to a heterogeneous catalyst for the oligomerization of ethylene or propylene. The heterogeneous catalyst comprises sulfate modified nickel on titanium modified alumina and a surface modification with yttrium (Y).

Another aspect of this disclosure is related to a composition comprising the heterogeneous catalyst as described herein and ethylene monomer or propylene monomer and/or an oligomer comprising one or more of a butene, hexene, octene, or a heavier olefinic compound, derivatives thereof or any combination thereof.

Another aspect of this disclosure is related to a method for processing the heterogeneous catalyst used in these processes for catalytic oligomerization of ethylene and propylene monomers. The method comprises activating the catalyst, wherein the activating comprises providing the catalyst, contacting the catalyst with an oxidant, reducing agent or inert for at least one hour at about 200° C. and obtaining an activated catalyst; or regenerating the catalyst, wherein the regenerating comprises providing the catalyst, contacting the catalyst with nitrogen for at least about 30 minutes at about 200° C. or greater temperature, and optionally contacting said catalyst with an oxidant or inert, and obtaining a regenerated heterogeneous catalyst.

Yet another aspect of this disclosure is related to a method for manufacturing a catalyst. The method comprises dissolving titanium butoxide in alcohol solvent, adding alumina, calcinating in air, submerging the alumina in aqueous nickel sulfate/yttrium nitrate to form a catalyst, drying the catalyst, calcinating the catalyst; and recovering the catalyst.

DETAILED DESCRIPTION

Figure 1:
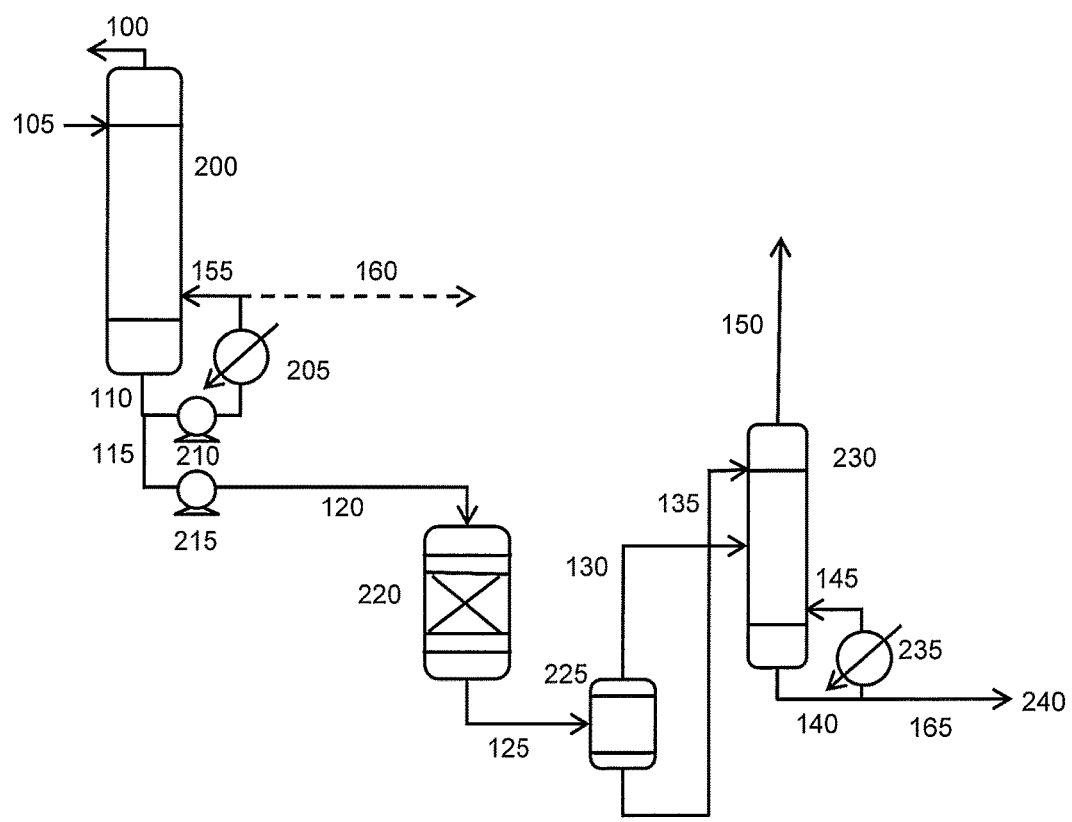
FIG. 1 is a schematic of an exemplary process for the conversion of ethylene in a dilute ethylene stream into oligomer, using a heterogeneous catalyst comprising sulfate modified nickel on titanium modified alumina, and a surface modification with yttrium (Y).

All references referred to are incorporated herein by reference in their entireties.

Unless specifically defined otherwise, all technical and scientific terms used herein have the same meaning as commonly understood by one of ordinary skill in the art to which this disclosure belongs. Unless mentioned otherwise, the techniques employed or contemplated herein are standard methodologies well known to one of ordinary skill in the art. The practice of the present disclosure will employ, unless otherwise indicated, conventional techniques of chemistry and engineering, which are within the skill of the art. The materials, methods and examples are illustrative only and not limiting. The following is presented by way of illustration and is not intended to limit the scope of the disclosure. Before the present embodiments are described, it is to be understood that the present disclosure is not limited to the particular processes, catalysts and systems described, as these may vary. It is also to be understood that the terminology used in the description is for the purpose of describing the particular versions or embodiments only. Process flow diagrams are provided herein, as exemplary but non-limiting illustrations of the general process. Certain derivations are known to those skilled-in-the-art, such as further integration with conventional recovery equipment, various heat integration options and product stabilization schemes. Many modifications and other embodiments of the disclosures set forth herein will come to mind to one skilled in the art to which these disclosures pertain having the benefit of the teachings presented in the descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

It is known in the art that in conventional processes a steam cracker (gas cracker) utilizes feedstock comprising, typically, ethane or naphtha. Such ethane or naphtha is known to be thermally cracked at elevated temperature in multiple parallel furnaces in the presence of steam. Thermal cracking converts the feedstock to a combination of olefins, including ethylene and propylene, as well as unconverted feedstock, paraffin materials (e.g., ethane, propane, etc.) and heavier components. The product of conventional cracking can be provided to a separation zone and purification zone in such conventional systems, to remove water, light and heavy products and to isolate and purify desired products, such as ethylene and propylene. In such systems, ethane, for example, obtained from the base of the $C_2$ splitter column is recycled to the cracking furnaces to provide feedstock. Typically, such recycled ethane contains some ethylene however, when the ethane is material is recycled it is converted to coke and gas in the cracking furnace, resulting in a yield loss, and causing the furnace to foul. Accordingly, conventional cracking furnaces are typically subjected to a decoking process on a periodic basis, resulting in downtime. In conventional propane dehydrogenation systems, the feedstock is propane, which is catalytically dehydrogenated to propylene. The dehydrogenation process is endothermic, with heat being provided by the catalyst substrate. Typically, carbon accumulates on the surface of the catalyst as a result of coking reactions, which leads to a loss of catalyst activity. In such conventional processes, the catalyst is periodically regenerated by use of gas, provided at elevated temperature. The regeneration process burns-off the carbon deposits from the catalyst surface, and heats the catalyst substrate, thereby providing heat for the next reaction stage. In such conventional systems, excessive coke formation leads to a more rapid deterioration of catalyst performance and the need for more frequent catalyst regeneration, causing more downtime and reducing the yield of propylene. In such systems, products from the dehydrogenation process are fed to a separation and purification section to isolate and purify the main product, which is polymer grade propylene. Propylene is purified by distillation in a C3 splitter distillation column, in which polymer grade propylene product is removed from the top of the distillation column, whilst residual unconverted propane is removed from the base of the column and recycled. Such conventional C3 splitter separation is difficult and expensive, as the boiling points of propylene and propane are relatively close, thus many separating plates are typically required within such distillation column whereas the production of propylene is significant (a large diameter column is necessary to accommodate capacity). See, for example, the C3 splitter for propane dehydrogenation measuring 28 feet in diameter and about 300 feet tall described in "Digital Refining, Troubleshooting a C3 splitter tower Part 1: evaluation, October 2014. This problem is exacerbated by plant uprate projects, wherein the quality of the propylene produced from the C3 splitter is maintained by allowing additional propylene to slip into the recycled propane streams causing the carbon formation to accelerate with the associated problems highlighted above (see, Yee, et al., SENSITIVITY STUDY OF THE PROPANE DEHYDROGENATION PROCESS IN AN INDUSTRIAL RADIAL MOVING BED REACTOR, Journal of Engineering Science and Technology, Special Issue on SOMCHE 2014 & RSCE 2014 Conference, January (2015) 62-74, incorporated herein by reference in its entirety).

In general, this document provides, according to certain embodiments, processes for converting ethylene and propylene into a butene, hexene, octene, or heavier olefinic compounds. The processes utilize a heterogeneous catalyst comprising sulfate modified nickel on titanium modified alumina, and a surface modification with yttrium (Y) for the conversion of ethylene and/or propylene into one or more oligomers. The resulting oligomer product produced may be used for the manufacture of a variety of chemical products, as a component in the gasoline pool, or for use as feedstock for the manufacture of polyolefins, lubricants, oils or detergents.

In general, the present disclosure relates to improved, economically advantageous processes for the catalytic oligomerization of ethylene and propylene into a butene, hexene, octene, or heavier olefinic compounds utilizing a robust heterogeneous catalyst. Thus, the presently disclosed processes allow for at least one of (1) high olefin conversion at relatively low operating temperatures, (2) enhanced catalyst utility and enhanced, superior cycle lifetime, (3) oligomer products comprised substantially of non-aromatic olefin compounds, (4) reduced catalyst fouling, (5) reduced yield losses, and (6) advantageous reactor cycle times.

In at least one embodiment, the catalyst reactors may be taken off-line from the processing of the monomers and regenerated periodically using nitrogen. One catalyst reactor may be operating while the other reactor is regenerated.

In accordance with the presently disclosed processes, the catalyst may be a heterogeneous catalyst for the oligomerization of ethylene or propylene comprising sulfate modified nickel on titanium modified alumina, and a surface modification with yttrium (Y). In one aspect of the present disclosure, the heterogeneous catalyst comprises sulfate modified nickel on gamma-alumina. In a preferred aspect, the heterogeneous catalyst comprises sulfate modified nickel on titanium modified alumina and has a surface modification with yttrium (Y), wherein the nickel to yttrium molar ratio is about 1:1 to 50:1. In another aspect of the disclosure, the nickel to yttrium molar ratio is about 1:1 to 40:1. In a further aspect, the nickel to yttrium molar ratio is about 1:1 to 30:1. A preferred aspect of the present disclosure is a heterogeneous catalyst comprising sulfate modified nickel on titanium modified alumina comprising a surface modification with yttrium (Y), wherein the nickel to yttrium molar ratio is about 1:1 to 25:1. In another aspect, the heterogeneous catalyst comprises an additional surface modification with at least one of cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), and ytterbium (Yb). In accordance with the presently disclosed process, the catalyst may be a heterogeneous catalyst on doped alumina.

In one aspect of the present disclosure, the heterogeneous catalyst is present in a composition. A composition of the present disclosure may, in one aspect, include ethylene monomer or propylene monomer and/or an oligomer comprising one or more of a butene, hexene, octene, or a heavier olefinic compound, derivatives thereof or any combination thereof. A composition of the present disclosure may, in one aspect, be liquid. Another aspect of the composition is a gasified liquid. Yet another aspect of the present disclosure is a substantially gaseous composition.

The heterogeneous catalyst of the present disclosure may provide a high conversion of ethylene or propylene at relatively low temperature, as compared to conventional processes. In one aspect of the present disclosure, the heterogeneous catalyst oligomerizes ethylene monomer and/or propylene monomer at liquid phase oligomerization condition temperature of less than about 50° C. Another aspect of the present disclosure is an oligomerization condition temperature of less than about 45° C. Yet another embodiment of the present disclosure is an oligomerization condition temperature of less than about 40° C. or less than about 35° C., 30° C., 25° C., 20° C., 15° C., 10° C., 5° C., or 0° C.

FIG. 1 depicts a process diagram for an exemplary conversion of ethylene (ethylene monomer) present in a stream (120) obtained from an existing C2 splitter (200). Ethylene monomer is purified by distillation in a C2 splitter (200), in which ethylene monomer is a product that is removed from the top (stream 100) of the distillation column (200), whilst residual unconverted ethane is removed from the base of the column. Stream (120) obtained using pump (215) provides ethylene monomer present in such stream to a reactor (220) of the present disclosure.

In conventional systems, ethane obtained from the base of the C2 splitter distillation column (200) is recycled to cracking furnaces as feedstock (160). Typically, such recycled ethane contains ethylene. In traditional systems known in the art, when stream (110) containing ethylene monomer is recycled (160), the ethylene is converted to coke and gas in the cracking furnace, resulting in a yield loss, and causing the furnace to foul with carbonaceous materials. In such systems, cracking furnaces are typically subjected to a decoking process on a periodic basis, which is disadvantageous (e.g., resulting in downtime). Further, in such systems the capacity of gas cracker systems is optimized, i.e., there is an addition of extra cracking furnaces, etc. Often, in such conventional systems, the capacity of the C2 splitter column (200) is stretched by allowing additional ethylene to be lost in the recycled ethane. Such conventional systems allow the composition of the ethylene product to be maintained with minimal changes to the relatively high cost C2 splitter column (200) thereby resulting in significant concentrations of ethylene monomer in recycled ethane (160) (e.g., more than about 3% or more). This approach results in a significant increase in, for example, ethylene recycling, coking and lower yields. An alternative traditional approach is to utilize complex, high cost heterogeneous catalysts, operating at high temperatures.

In one aspect of the present disclosure, stream (120) obtained from C2 splitter distillation column (200) comprises ethylene monomer and ethane. In one aspect of the present disclosure, stream (120) obtained from the existing C2 splitter distillation column (200) comprises ethylene monomer which is contacted with a heterogeneous catalyst comprising sulfate modified nickel on titanium modified alumina, and a surface modification with yttrium (Y) in at least one reactor (220). Accordingly, one aspect of the present disclosure is a process for the catalytic oligomerization (165) of an ethylene monomer present in a stream (120) comprising providing a first stream comprising ethylene monomer (120), providing a heterogeneous catalyst present in a reactor (220), and contacting stream (120) and heterogeneous catalyst under liquid phase oligomerization conditions, oligomerizing the ethylene monomer in the stream to produce an oligomer, the oligomer comprising one or more of a, butene, hexene, octene, or a heavier olefinic compound, derivatives thereof or any combination thereof; and optionally, providing an oligomer stream (165), wherein the concentration of oligomer in the oligomer stream is greater than the concentration of oligomer in stream (120). In a preferred aspect of the present disclosure an ethane containing stream comprising >1% ethylene (120) obtained from a C2 splitter on a gas cracker plant, is provided to the heterogeneous catalyst in a reactor (220) wherein the heterogeneous catalyst has sulfate modified nickel on alumina and a surface modification with yttrium (Y), and wherein the catalyst converts at least 90% of the ethylene to butenes or hexenes. Another aspect provides an oligomerization stream (135), wherein the oligomer is distilled (230) to allow for separation of, for example, butene or hexenes from the base of the distillation column (230), which can be exported to a gasoline pool, and wherein purified ethane is recycled (150) to a cracking furnace(s).

Figure 2:
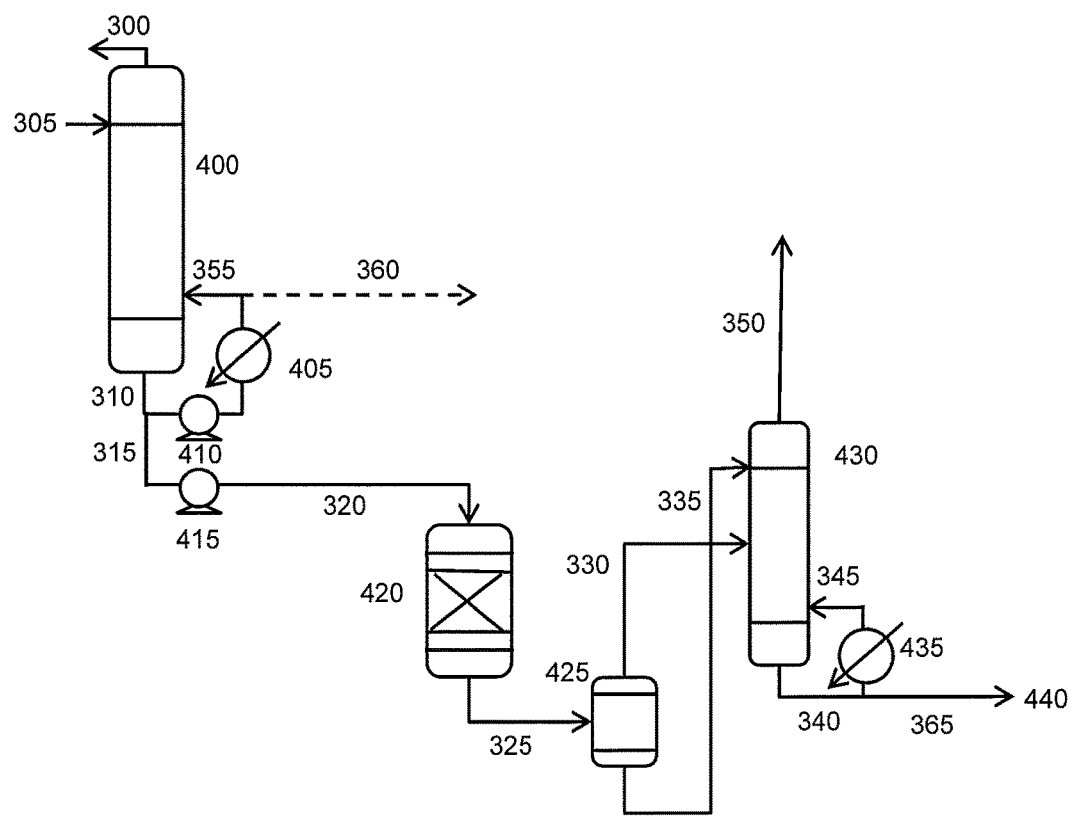
FIG. 2 is a schematic of an exemplary process for the conversion of propylene in a dilute propylene stream into oligomer, using a heterogeneous catalyst comprising sulfate modified nickel on titanium modified alumina, and a surface modification with yttrium (Y).

Yet another aspect of the present disclosure is a process for the catalytic oligomerization of propylene (propylene monomer). In one embodiment, the process for the catalytic oligomerization of propylene monomer comprises oligomerizing propylene monomer in a first stream to produce oligomer, or an oligomer stream, the oligomer comprising one or more of a, hexene, nonene, or a heavier olefinic compound, derivatives thereof or any combination thereof. In one aspect of the present disclosure, the oligomer comprising one or more of a hexene, nonene, or a heavier olefinic compound is present in an oligomer stream, wherein the concentration of oligomer in the oligomer stream is greater than the concentration of oligomer in the propylene monomer stream. FIG. 2 depicts a process diagram for an exemplary conversion of propylene monomer present in a stream (320) obtained from an existing C3 splitter (400). Propylene monomer is purified by distillation in a C3 splitter (400), in which propylene monomer is a product (300) that is removed from the top of the distillation column (400), whilst residual unconverted propane is removed from the base of the column. Stream (320), obtained using pump (415) provides propylene monomer, present in the stream to a reactor (420) of the present disclosure. In one aspect of the present disclosure, the stream (320) obtained from the existing C3 splitter distillation column (400) comprises propylene monomer and propane.

In comparison, in traditional systems, propane obtained from the base of the C3 splitter distillation column (400) is recycled to cracking furnaces as feedstock (360). Typically, such recycled propane contains some propylene. In traditional systems known in the art, when stream containing propylene monomer is recycled (360), the propylene is converted to coke and gas in the cracking furnace, resulting in a yield loss, and causing the furnace to foul with carbonaceous materials. In such systems, cracking furnaces are typically subjected to a decoking process on a periodic basis, which is disadvantageous (e.g., resulting in downtime). Further, in such systems the capacity of gas cracker systems are optimized, i.e., there is an addition of extra cracking furnaces, etc. Often, in such systems, the capacity of the C3 splitter column (400) is stretched by allowing additional propylene to be lost in the recycled propane. Such traditional systems allow the composition of the propylene product to be maintained with minimal changes to the relatively high cost C3 splitter column (400), thereby resulting in significant concentrations of propylene monomer in recycled propane (360) (e.g., more than about 2% or more). This conventional approach results in a significant increase in, for example, propylene recycling, coking and lower yields. An alternative traditional approach is to utilize complex, high cost heterogeneous catalysts, operating at high temperatures.

In one aspect of the present disclosure, stream (320) obtained from the existing C3 splitter distillation column (400) comprises propylene monomer, which is contacted with heterogeneous catalyst comprising sulfate modified nickel on titanium modified alumina, and a surface modification with yttrium (Y) in at least one reactor (420). Accordingly, one aspect of the present disclosure is a process for the catalytic oligomerization of propylene monomer present in a stream (320) comprising providing a stream comprising propylene monomer (320), providing the heterogeneous catalyst of the present disclosure in a reactor (420), and contacting stream (320) and the heterogeneous catalyst under oligomerization conditions, oligomerizing the propylene monomer in the stream to produce an oligomer, the oligomer comprising one or more of hexene, nonene, or a heavier olefinic compound, derivatives thereof or any combination thereof; and optionally, providing an oligomer stream (365).

A preferred embodiment of the present disclosure is a system and process, wherein a stream comprising about >1% propylene, obtained from a C3 splitter (400) on a propane dehydrogenation plant or a gas cracker, is provided to a heterogeneous catalyst wherein the heterogeneous catalyst has sulfate modified nickel on alumina and a surface modification with yttrium (Y) present in a reactor (420), wherein at least 90% of the propylene is converted into hexenes, nonenes or higher molecules and wherein simple distillation (430) is used to provide separation of oligomers from the base of the distillation column, which can be introduced into the gasoline pool and wherein the purified propane is recycled (440) to the dehydrogenation reactor or cracking furnaces.

In one aspect of the disclosure, the process comprises a heterogeneous catalyst comprising sulfate modified nickel on titanium modified alumina, and a surface modification with yttrium (Y), and at least one additional exchanged metal of lanthanide series. In another aspect of the disclosure, the process comprises a heterogeneous catalyst comprising a surface modification with at least one of cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm) and ytterbium (Yb). A preferred aspect of the present disclosure is a heterogeneous catalyst comprising a surface modification with at least yttrium (Y).

In one embodiment of the present disclosure, the catalyst is regenerated. A preferred aspect of the present disclosure is a catalyst regeneration process, wherein nitrogen, or other inert gas, is provided to the catalyst under conditions suitable for regeneration of the catalyst. In one aspect, the inert gas is about 350° C. to 420° C. In one embodiment, regeneration occurs for about one hour. In another embodiment, regeneration occurs for about two hours to about six hours. In one aspect, nitrogen flow is determined such that the gas volume hourly space velocity of the nitrogen through the catalyst bed is set at least 100-5,000/hr, and in another aspect of the disclosure 500-1,000/hr.

In one aspect, the catalyst of the present disclosure has superior cycle time maintaining a high rate of olefin conversion per pass. In one aspect of the present disclosure, the catalyst cycle time is over 1,000 hours accompanied by greater than 75% conversion. In another aspect, the catalyst cycle time is 1,500 hours accompanied by greater than 75% conversion; or 2,000 hours accompanied by greater than 75% conversion; or 2,500 hours accompanied by greater than 75% conversion.

An aspect of the present disclosure is a relatively low temperature oligomerization process. A preferred aspect is an oligomerization process at a temperature of about <30° C. Oligomerized product obtained from the present disclosure is optionally separated using conventional fractional distillation or other separation methods.

EXAMPLES

An example of preparation of a catalyst useful in conjunction with the materials and methods of the present disclosure is provided in Example 1. Process performance of the oligomerization catalyst is provided by Examples 2 and 3.

Example 1

Titanium butoxide $Ti(OCH_2CH_2CH_2CH_3)_4$ is dissolved in alcohol solvent and added dropwise to an alumina, followed by calcination in air to at least 500° C. Following calcination, the Ti modified alumina is submerged in an aqueous solution of nickel sulfate/yttrium nitrate, where it is allow to rest for at least 2 hours. After solution impregnation, the catalyst is dried in air, and then calcined to at least 500° C. The resulting catalyst has a nickel content of at least 8.0 wt % with a Ni/Y molar ratio of 25.

Example 2

Catalytic performance evaluation of the olefin oligomerization catalyst of Example 1 was carried out using a PLC controlled fixed bed testing unit. Precise gas feed was delivered using Brooks 5850 mass flow controllers. Liquefied petroleum gas (LPG) feed was delivered using a Teledyne Isco 500D syringe pump. Reactor pressure was maintained by a Badger research control valve. The entire product effluent was analyzed using an Agilent 7890 GC equipped with dual FIDs. Olefin conversion was determined by comparing the reactor feed input versus reactor product output. Product composition was confirmed by the use of pure calibration standards and comparing retention times to the unknown peaks in the chromatograms.

Figure 3:
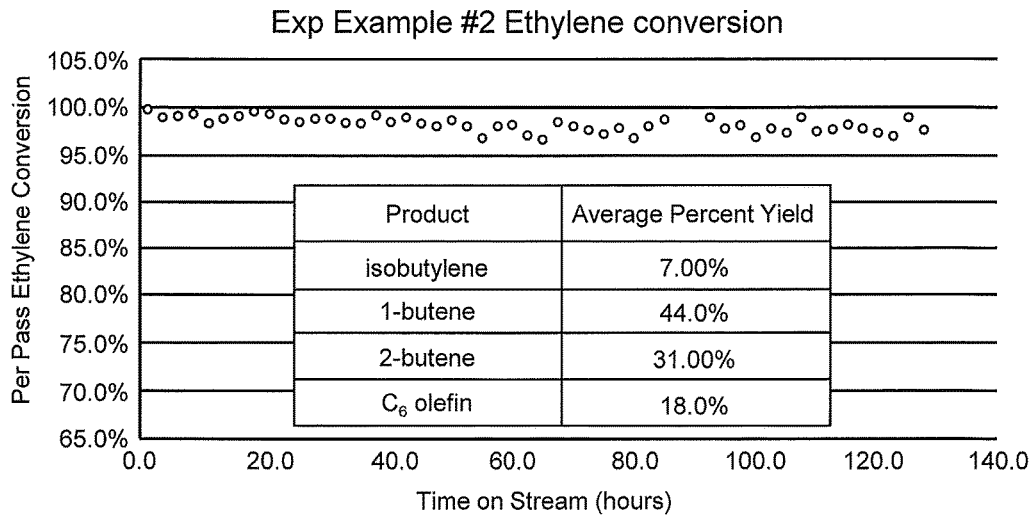
FIG. 3 illustrates ethylene conversion and resulting product composition utilizing the catalyst of Example 1 in the process described in Example 2.

6 mL of 16 mesh catalyst was placed in a 7.5 mm i.d. 316 SS u-tube reactor and submerged in a fluidized sand bath heater. The catalyst was purged with 20 liters/hour of 25 psig hot dry nitrogen at 420° C. for 6 hours and then cooled to 25° C. under constant nitrogen flow. Once cool, the nitrogen pressure was increased to 350 psig. Once at pressure, the nitrogen was stepwise removed from the feed accompanied by simultaneous introduction of 6 mL/hour of a 3 wt % ethylene in propane LPG feed. The catalyst was subjected to this constant feed condition for 125 hours. Ethylene conversion and product composition are presented in FIG. 3.

Example 3

Catalytic performance evaluation of the olefin oligomerization catalyst of Example 1 was carried out using a PLC controlled fixed bed testing unit. Precise gas feed was delivered using Brooks 5850 mass flow controllers. Liquefied petroleum gas (LPG) feed was delivered using a Teledyne Isco 500D syringe pump. Reactor pressure was maintained by a Badger research control valve. The entire product effluent was analyzed using an Agilent 7890 GC equipped with dual FIDs. Olefin conversion was determined by comparing the reactor feed input versus reactor product output. Product composition was confirmed by the use of pure calibration standards and comparing retention times to the unknown peaks in the chromatograms.

Figure 4:
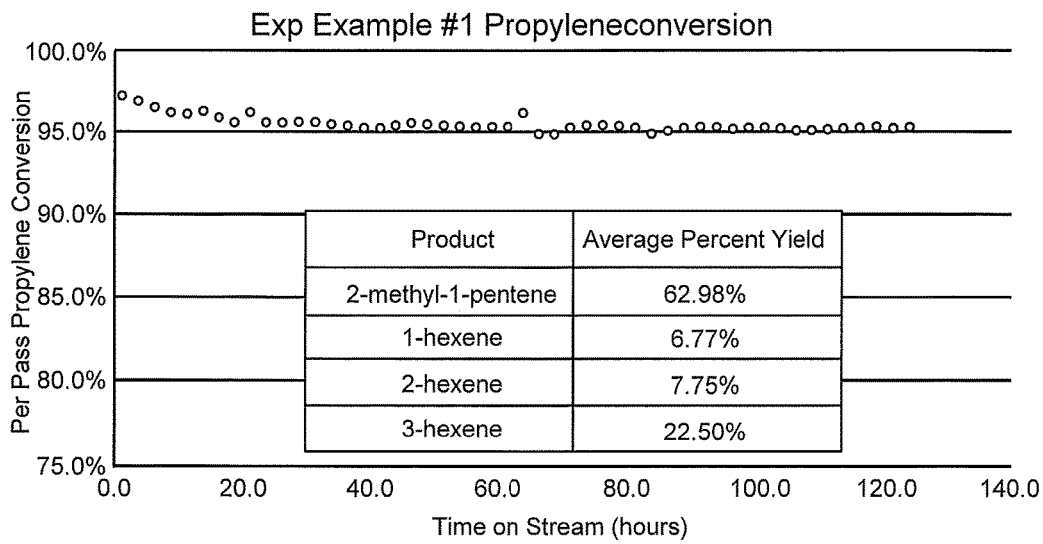
FIG. 4 illustrates propylene conversion and resulting product composition utilizing the catalyst of Example 1 in the process described in Example 3.

6 mL of 16 mesh catalyst was placed in a 7.5 mm i.d. 316 SS u-tube reactor and submerged in a fluidized sand bath heater. The catalyst was purged with 20 liters/hour of 25 psig hot dry nitrogen at 420° C. for 6 hours and then cooled to 25° C. under constant nitrogen flow. Once cool, the nitrogen pressure was increased to 350 psig. Once at pressure, the nitrogen was stepwise removed from the feed accompanied by simultaneous introduction of 6 mL/hour of a 3 wt % propylene in propane LPG feed. The catalyst was subjected to this constant feed condition for 125 hours. Propylene conversion and product composition are presented in FIG. 4.

LITERATURE REFERENCES

Digital Refining, Troubleshooting a C3 splitter tower Part 1: evaluation, October 2014.

Yee, et al., SENSITIVITY STUDY OF THE PROPANE DEHYDROGENATION PROCESS IN AN INDUSTRIAL RADIAL MOVING BED REACTOR, Journal of Engineering Science and Technology, Special Issue on SOMCHE 2014 & RSCE 2014 Conference, January (2015) 62-74.

What is claimed is:

1. A process for the catalytic oligomerization of an ethylene monomer comprising:
   providing a first stream comprising ethane and ethylene monomer;
   providing a heterogeneous catalyst, the heterogeneous catalyst comprising sulfate modified nickel on titanium modified alumina, and a surface modification with yttrium (Y);
   contacting the first stream and the heterogeneous catalyst under oligomerization conditions;
   oligomerizing the ethylene monomer in the first stream to produce an oligomer, the oligomer comprising one or more of a butene, hexene, octene, or a heavier olefinic compound, derivatives thereof or any combination thereof; and
   optionally, providing an oligomer stream, wherein the concentration of oligomer in the oligomer stream is greater than the concentration of oligomer in the first stream.

2. A process for the catalytic oligomerization of a propylene monomer comprising:
   providing a first stream comprising propane and propylene monomer;
   providing a heterogeneous catalyst, the heterogeneous catalyst comprising sulfate modified nickel on titanium modified alumina, and a surface modification with yttrium (Y);
   contacting the first stream and the heterogeneous catalyst under oligomerization conditions;
   oligomerizing the propylene in the first stream to produce an oligomer, the oligomer comprising one or more of a hexene, nonene, or a heavier olefinic compound, derivatives thereof or any combination thereof; and
   optionally, providing an oligomer stream, wherein the concentration of oligomer in the oligomer stream is greater than the concentration of oligomer in the first stream.

3. The process of claim 1 or claim 2, wherein the first stream:
   (i) comprises less than about 70% monomer; or
   (ii) the stream is a dilute monomer stream.

4. The process of claim 1 or claim 2, wherein the alumina:
   (i) comprises a gamma alumina; or
   (ii) is a gamma alumina.

5. The process of claim 1 or claim 2, wherein the concentration of oligomer in the oligomer stream is about 100% or less.

6. The process of claim 1 or claim 2, wherein the contacting occurs in a heterogeneous reactor, a continuous reactor, a fixed bed plug flow reactor or a continuous stirred tank reactor, fluidized bed reactor or reactive distillation system, or combinations thereof.

7. The process of claim 1 or claim 2, wherein the nickel to yttrium molar ratio is from about 1:1 to about 50:1.

8. The process of claim 1 or claim 2, wherein the oligomer is linear, branched, or a combination thereof.

9. The process of claim 1 or claim 2, wherein the oligomerization conditions comprise at least one of:
   (a) a temperature of less than about 50° C., and
   (b) a liquid phase.

10. A heterogeneous catalyst for the oligomerization of ethylene or propylene comprising sulfate modified nickel on titanium modified alumina and a surface modification with yttrium (Y).

11. A composition comprising the catalyst of claim 10 and:
    (i) ethylene monomer or propylene monomer and/or
    (ii) an oligomer comprising one or more of a butene, hexene, octene, or a heavier olefinic compound, derivatives thereof or any combination thereof.

12. A method for processing the catalyst of claim 1 or 2, comprising:
    (a) activating the catalyst, the activating comprising:
        (i) providing the catalyst,
        (ii) contacting the catalyst with an oxidant, reducing agent or inert for at least one hour at about 200° C.; and
        (iii) obtaining an activated catalyst, or
    (b) regenerating the catalyst, the regenerating comprising
        (i) providing the catalyst,
        (ii) contacting the catalyst with nitrogen for at least about 30 minutes at about 200° C. or greater temperature, and optionally contacting said catalyst with an oxidant or inert; and
        (iii) obtaining a regenerated heterogeneous catalyst.

* * * * *